United States Patent
Murakami et al.

(10) Patent No.: US 10,420,959 B2
(45) Date of Patent: Sep. 24, 2019

(54) ENERGY DEGRADER, CHARGED PARTICLE BEAM EMISSION SYSTEM PROVIDED WITH SAME, AND METHOD OF PRODUCING GRAPHITE FILM

(71) Applicant: Kaneka Corporation, Osaka (JP)

(72) Inventors: Mutsuaki Murakami, Osaka (JP); Atsushi Tatami, Osaka (JP); Masamitsu Tachibana, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 15/779,656

(22) PCT Filed: Nov. 30, 2016

(86) PCT No.: PCT/JP2016/085624
§ 371 (c)(1),
(2) Date: May 29, 2018

(87) PCT Pub. No.: WO2017/094802
PCT Pub. Date: Jun. 8, 2017

(65) Prior Publication Data
US 2018/0256918 A1    Sep. 13, 2018

(30) Foreign Application Priority Data

Nov. 30, 2015    (JP) .................. 2015-234006

(51) Int. Cl.
*G21K 5/04*    (2006.01)
*A61N 5/10*    (2006.01)

(52) U.S. Cl.
CPC ............. *A61N 5/1077* (2013.01); *A61N 5/10* (2013.01); *G21K 5/04* (2013.01); *A61N 2005/1087* (2013.01); *A61N 2005/1095* (2013.01)

(58) Field of Classification Search
CPC .... A61N 2005/1087; A61N 2005/1095; A61N 5/10; G21K 5/04
See application file for complete search history.

(56) References Cited

U.S. PATENT DOCUMENTS 5,042,059 A * 8/1991 Watanabe .............. B82Y 10/00
                                                    378/145
6,462,348 B1 * 10/2002 Gelbart ................ G21K 1/093
                                                    250/505.1

(Continued)

FOREIGN PATENT DOCUMENTS

CN    104445174 A    3/2015
JP    H1286300 A    11/1989

(Continued)

OTHER PUBLICATIONS

Bylinskii, I., and M. K. Craddock. "The TRIUMF 500 MeV cyclotron: the driver accelerator." Hyperfine Interactions 225.1-3 (2014): 9-16 (Year: 2014).*

(Continued)

*Primary Examiner* — Wyatt A Stoffa
(74) *Attorney, Agent, or Firm* — Osha Liang LLP (57) ABSTRACT

Provided is an energy degrader including an attenuation member that becomes radioactive only to a lesser extent than conventional attenuation members. An attenuation member (11) is a graphite film, the graphite film has a thermal conductivity, in a surface direction, of 1200 W/(m·K) or greater, and the graphite film has a thickness of 0.1 μm or greater and 50 μm or less.

12 Claims, 2 Drawing Sheets (56) References Cited

U.S. PATENT DOCUMENTS

| | | | |
|---|---|---|---|
| 9,807,878 B2* | 10/2017 | Tatami | B32B 9/007 |
| 2002/0179854 A1* | 12/2002 | Tsukihara | G21K 1/08 |
| | | | 250/492.2 |
| 2003/0128811 A1* | 7/2003 | Verman | G21K 1/06 |
| | | | 378/84 |
| 2012/0034151 A1 | 2/2012 | Nishikawa et al. | |
| 2013/0189180 A1* | 7/2013 | Ohta | C09K 5/14 |
| | | | 423/448 |
| 2013/0197608 A1* | 8/2013 | Eiger | A61N 1/37 |
| | | | 607/61 |
| 2013/0209732 A1* | 8/2013 | Nishikawa | H05K 7/20509 |
| | | | 428/138 |
| 2013/0299721 A1 | 11/2013 | Sasai | |
| 2014/0091238 A1* | 4/2014 | Miyashita | G21K 1/10 |
| | | | 250/492.3 |
| 2014/0147648 A1 | 5/2014 | Zhamu et al. | |
| 2015/0170780 A1* | 6/2015 | Miyashita | G21K 1/10 |
| | | | 250/396 R |
| 2016/0059444 A1* | 3/2016 | Wang | C01B 31/04 |
| | | | 423/448 |
| 2016/0249453 A1 | 8/2016 | Tatami et al. | |
| 2016/0279900 A1* | 9/2016 | Fujiwara | H01L 23/3735 |
| 2016/0314929 A1* | 10/2016 | Drees | G21K 1/093 |
| 2017/0007848 A1* | 1/2017 | Drees | H01J 37/14 |
| 2017/0053851 A1* | 2/2017 | Kutsumizu | H01L 23/373 |
| 2017/0182336 A1* | 6/2017 | Cruz | D21H 27/002 |
| 2017/0203127 A1* | 7/2017 | Dolney | A61N 5/1071 |
| 2017/0267908 A1* | 9/2017 | Murakami | G21K 5/08 |
| 2017/0324110 A1* | 11/2017 | Fujii | H01M 10/48 |
| 2018/0010028 A1* | 1/2018 | Zhamu | C09K 5/14 |
| 2018/0049306 A1* | 2/2018 | Murakami | B32B 9/007 |
| 2018/0133514 A1* | 5/2018 | Mansfield | A61N 5/1077 |
| 2018/0135200 A1* | 5/2018 | Zhamu | C30B 5/00 |
| 2018/0144843 A1* | 5/2018 | Zhamu | H01B 1/04 |
| 2018/0164704 A1* | 6/2018 | Jacobs | G03F 7/70783 |
| 2019/0002278 A1* | 1/2019 | Lin | B82Y 30/00 |

FOREIGN PATENT DOCUMENTS

| | | |
|---|---|---|
| JP | H0421508 A | 1/1992 |
| JP | 2006142315 A | 6/2006 |
| JP | 2008194441 A | 8/2008 |
| JP | 2011063509 A | 3/2011 |
| JP | 2012249940 A | 12/2012 |
| JP | 2013238515 A | 11/2013 |
| JP | 5726541 B2 | 6/2015 |
| WO | 2015045641 A1 | 4/2015 |
| WO | 2015072487 A1 | 5/2015 |

OTHER PUBLICATIONS

Pyrolytic Graphite Sheet Evolves to Meet Tough Thermal Demands, Electronic Design, Oct. 2015 (Year: 2015).*
Slack, Glen A. "Anisotropic thermal conductivity of pyrolytic graphite." Physical Review 127.3 (1962): 694. (Year: 1962).*
International Search Report issued in International Application No. PCT/JP2016/085624; dated Feb. 7, 2017 (2 pages).
International Preliminary Report on Patentability issued in International Application No. PCT/JP2016/085624; dated Jun. 14, 2018 (7 pages).
Kaneka: "Graphinity Typical Properties", Jun. 30, 2012, XP055597675, Retrieved from the Internet (1 page).
Kaneka: "Graphnity", Mar. 28, 2014, XP055597679, Retrieved from the Internet (1 page).
Keikikaku: "PGS" Graphite Sheets, Nov. 7, 2015, XP055556674, Retrieved from the Internet (10 pages).
Partial Supplementary European Search Report issued in European Application No. 16870739.6, dated Jun. 28, 2019 (19 pages).
Office Action issued in Japanese Application No. 2017-554158; dated May 7, 2019 (7 pages).

* cited by examiner

ENERGY DEGRADER, CHARGED PARTICLE BEAM EMISSION SYSTEM PROVIDED WITH SAME, AND METHOD OF PRODUCING GRAPHITE FILM

TECHNICAL FIELD

The present invention relates to an energy degrader, a charged particle emission system that includes the energy degrader, and a method of producing a graphite film.

BACKGROUND ART

In the fields of accelerators to accelerate charged particles, beam blocking devices are known, such as stoppers to stop charged particles of an accelerated beam and energy degraders to degrade the energy (speed) of charged particles.

An example of equipment using an accelerator is positron therapy equipment configured to treat cancer by irradiating a patient with a charged particle beam such as a proton beam. Such equipment includes: a cyclotron to accelerate ions (charged particles) generated by an ion source; a transport line to transport the charged particles accelerated by the cyclotron; and a freely rotatable emission device (rotatable gantry) to emit the charged particles toward a patient from a desired direction.

For example, Patent Literature 1 discloses a degrader which is constituted by a beam absorber (attenuation member) placed in a beam line (transport line) and which thereby attenuates beam energy.

A charged particle beam, such as a proton beam, travels inside a substance to a certain depth that depends on its energy, and has the maximum radiation dose at that depth. Therefore, in positron therapy, the energy of the charged particle beam is adjusted according to the to-be-irradiated position (depth) of an irradiation target (patient), and thus it is necessary to degrade the energy (speed) of the charged particle beam with the use of an energy degrader and cause the beam to have the maximum radiation dose at an optimal depth (cancer area). Patent Literatures 2 and 3 each disclose an energy degrader, having an attenuation member, which is for use in such adjustment of the charged particle beam.

CITATION LIST

Patent Literature

[Patent Literature 1]
Japanese Patent Application Publication, Tokukaihei, No. 1-286300
[Patent Literature 2]
Specification of Japanese Patent No. 5726541
[Patent Literature 3]
Japanese Patent Application Publication, Tokukai, No. 2012-249940

SUMMARY OF INVENTION

Technical Problem

Generally, as an attenuation member for an energy degrader, a film made of a metal such as titanium is often used from the viewpoint of durability and heat resistance, or a carbon material is often used from the viewpoint that the carbon materials do not easily become radioactive. However, there is an issue in that, even in a case where the attenuation member is constituted by a carbon material such as graphite, the extent of radioactivation cannot be sufficiently reduced. The attenuation member, which has become highly radioactive, cannot be handled by humans. Therefore, it is necessary to stop the accelerator and replace the attenuation member before the attenuation member becomes too radioactive. This leads to a substantial decrease in operating time of the accelerator.

One embodiment of the present invention was made in view of the above issue, and an object thereof is to obtain an energy degrader including an attenuation member that is sufficiently durable and heat-resistant and that can reduce the extent of radioactivation, a charged particle emission system including the energy degrader, and a method of producing a graphite film.

Solution to Problem

In order to attain the foregoing object, an energy degrader in accordance with one aspect of the present invention is an energy degrader including one or more attenuation members configured to attenuate energy of a charged particle beam incident thereon, wherein at least one of the one or more attenuation members is a graphite film placed such that the charged particle beam is incident on a surface thereof, the graphite film has a thermal conductivity, in a surface direction, of 1200 W/(m·K) or greater, and the graphite film has a thickness of 0.1 μm or greater and 50 μm or less.

An energy degrader in accordance with a further aspect of the present invention is an energy degrader including an attenuation structure constituted by a plurality of attenuation members each configured to attenuate energy of a charged particle beam incident thereon, the attenuation structure having a multilayer structure composed of the plurality of attenuation members stacked together along a thickness direction, the plurality of attenuation members being constituted by graphite films each placed such that the charged particle beam is incident on a surface thereof.

In order to attain the foregoing object, a method of producing a graphite film in accordance with still a further aspect of the present invention is a method of producing a graphite film for use as an attenuation member of an energy degrader, the method including firing a polymeric film at a temperature of 2400° C. or above to obtain the graphite film.

Advantageous Effects of Invention

One embodiment of the present invention provides the following effect: it is possible to reduce the extent of radioactivation of an attenuation member as compared to conventional techniques.

DESCRIPTION OF EMBODIMENTS

As described earlier, a carbon material such as graphite, which is said to become radioactive to a relatively small extent, has been conventionally used as an attenuation member to degrade the energy of charged particles. However, the inventors found on their own that, even in a case where graphite is used as a raw material to prepare an attenuation member, there may be cases where the extent of radioactivation cannot be sufficiently reduced, depending on the energy of charged particles. This issue has never been mentioned in the technical field to which the present invention belongs, and can be said to be a new issue. In addition, during the attenuation of the kinetic energy of charged particles, the attenuation member experiences a very large heat load. In view of this, the inventors worked hard in an attempt to develop an attenuation member that becomes radioactive to a lesser extent and that can also sufficiently withstand the above-mentioned heat load.

As a result, the inventors succeeded in developing an attenuation member that can reduce the extent of radioactivation and that can sufficiently withstand the heat load, by employing graphite having specific properties and certain dimensions. Specifically, the inventors made the following novel finding: it is possible to solve the foregoing issue by employing a graphite film whose thermal conductivity in a surface direction is equal to or greater than a certain value and whose thickness falls within a certain range. On the basis of this finding, the inventors accomplished the present invention.

Usually, when the thickness of a graphite film is reduced, the physical strength of the graphite film decreases. Therefore, it appears that reducing the thickness of a graphite film is in a trade-off relationship with an improvement in collision stopping power of an attenuation member for a charged particle. Furthermore, since a large heat load is generated during attenuation of the kinetic energy of charged particles, it would be usual to think that a thin graphite film cannot withstand this heat load. In addition, it is very difficult in the first place to produce a thin graphite film that has excellent properties such as excellent thermal conductivity, excellent electric conductivity, and excellent folding endurance.

The inventors, however, did several researches on their own and established a technique to produce a graphite film that is thin and that has excellent properties such as excellent thermal conductivity. The inventors did a further research and newly found that, surprisingly, this graphite film can reduce the extent of radioactivation and can also withstand the heat load generated during the attenuation of the energy of charged particles. The technical idea of the present invention based on the above finding is not the one that is predictable from conventional findings, but the one that has been accomplished by the inventors themselves.

In a case where the intensity of a charged particle beam such as an ion beam is to be controlled at a desired intensity, it is preferable that the thickness of the graphite film, through which the beam passes, is precisely controlled. The present invention is flexibly applicable to every thickness, and thus provides an excellent method.

Figure 1:
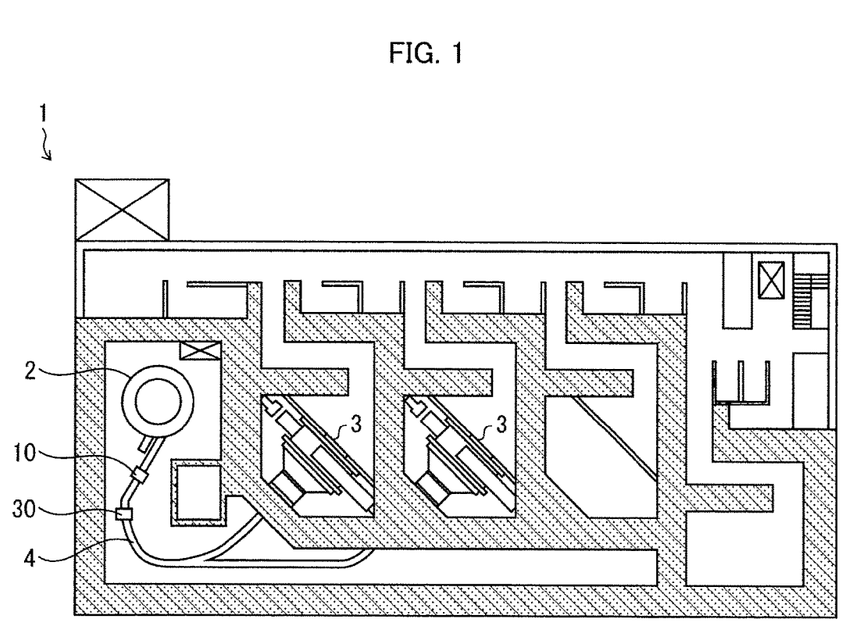
FIG. 1 is a layout drawing illustrating a configuration of a particle beam therapy system 1 in accordance with an embodiment of the present invention.

The following description will discusses an embodiment of the present invention in detail. The present embodiment discusses a case in which a charged particle emission system is a particle beam therapy system. FIG. 1 is a layout drawing illustrating a configuration of a particle beam therapy system in accordance with the present embodiment.

(Configuration of Charged Particle Emission System)

A particle beam therapy system 1 is for use in, for example, cancer treatment, and is an apparatus configured to emit a proton beam (charged particle beam) toward a tumor (irradiation target) inside the body of a patient.

As illustrated in FIG. 1, the particle beam therapy system 1 includes: a cyclotron (particle accelerator) 2 configured to generate a proton beam by accelerating ions (positive ion of hydrogen) generated at an ion source (not illustrated); a freely rotatable gantry (emission device) 3 configured to emit the proton beam toward a patient from a desired direction; and a transport line 4 configured to transport the proton beam generated at the cyclotron 2 (charged particle beam accelerated at the cyclotron) to the rotatable gantry 3.

The proton beam accelerated at the cyclotron 2 is deflected along the transport line 4 and is transported to the rotatable gantry 3. The transport line 4 is provided with a bending magnet to deflect the proton beam. The transport line 4 is further provided with an energy degrader 10, which is configured to attenuate the energy of charged particles. The configuration of the energy degrader 10 will be described later.

The transport line 4 is further provided with an energy selection system (ESS) 30, which is provided in a stage subsequent to (downstream of) the energy degrader 10. The ESS 30 is configured to selectively obtain a proton beam with a desired energy width from the received proton beam having a certain energy distribution. At the ESS 30, the selection is carried out so that the energy width of the resulting proton beam is within a desired range.

The rotatable gantry 3 includes an emission section configured to emit a proton beam toward a patient and toward a treatment table on which the patient lies. The charged particle beam, whose energy has been attenuated by the energy degrader 10, is emitted from the emission section toward a target region of the patient.

(Configuration of Energy Degrader 10)

Figure 2:
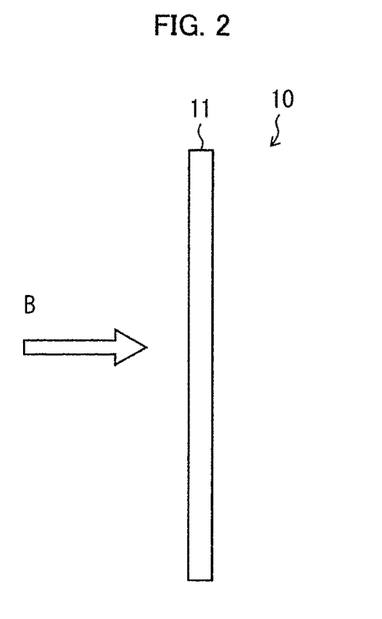
FIG. 2 schematically illustrates an energy degrader in accordance with an embodiment of the present invention.

FIG. 2 schematically illustrates the energy degrader in accordance with the present embodiment. The energy degrader 10 illustrated in FIG. 2 is provided in the path (beam line) of a proton beam B and is configured to attenuate the energy of the proton beam B.

The energy degrader 10 includes an attenuation member 11, which attenuates the energy of the proton beam B passing through the attenuation member 11. The attenuation member 11 is constituted by a graphite film. As illustrated in FIG. 2, the graphite film is placed such that the charged particle beam is incident on a surface of the graphite film, preferably placed such that the surface of the graphite film is perpendicular to the incident direction of the proton beam B. As used herein, the term "perpendicular" means that the angle between the graphite film and the incident direction of the proton beam B is a right angle within the measurement limits imposed by a measurement installment used in measuring the angle. It should be noted that the attenuation member 11 may either have a single-layer structure or a multilayer structure, although this is not illustrated in FIG. 2 for simplicity.

The attenuation member 11 is integrally supported by a support member (not illustrated). The energy degrader 10 further includes: a driving source (for example, a drive motor) configured to apply a driving force to the attenuation member 11; a guide means (for example, a guide rail) configured to guide the movement of the attenuation member 11; and/or the like.

The energy degrader 10 attenuates the energy of the proton beam B by moving, into the path of the proton beam B, the attenuation member 11 through which the proton beam B passes.

The energy degrader 10 may be constituted by a plurality of separate attenuation members 11. In this case, the plurality of attenuation members 11 have respective different thicknesses. The energy degrader 10 in this case is configured to attenuate the energy of the proton beam B to an extent that differs depending on the thickness of each attenuation member 11.

(Function of Particle Beam Therapy System 1)

The particle beam therapy system 1 is arranged such that a proton beam B is accelerated by the cyclotron 2 and the accelerated proton beam B (which has an energy range of, for example, 230 MeV±several MeV) is introduced into the energy degrader 10. At the energy degrader 10, the attenuation member 11 is driven and moved by a driving means, and the attenuation member 11 is placed in the path of the proton beam B. When the proton beam B passes through the attenuation member 11, the proton beam B is decelerated by the attenuation member 11 and the energy thereof is attenuated by the attenuation member 11 (attenuated to, for example, 200 MeV±a dozen or so MeV).

The proton beam B, which has passed through the energy degrader 10, is introduced into the ESS 30. At the ESS 30, a proton beam B having a desired energy range (for example, 200 MeV±1 MeV) is selectively obtained from the introduced proton beam B. The proton beam B, which has a selected energy range, is transported and introduced into the rotatable gantry 3 via the transport line 4, and emitted toward an irradiation target. In this way, the proton beam B is emitted so that the proton beam B is delivered to a position at a certain depth in the irradiation target.

(Regarding Attenuation Member 11)

It is only necessary that the graphite film constituting the attenuation member 11 have a thermal conductivity, in a surface direction, of 1200 W/(m·K) or greater and have a thickness of 0.1 µm or greater and 50 µm or less. The other configurations of the graphite film are not particularly limited. Such a graphite film is preferred, because such a graphite film has a high strength and a high thermal conductivity. The term "thickness" in the above description means a dimension of the attenuation member 11 along the direction in which a charged particle beam passes through the attenuation member 11. The attenuation member 11 may be adjusted to have a desired thickness by stacking a plurality of graphite films of the same thickness or of different thicknesses together. For example, in a case where the thickness of the attenuation member 11 is 40 µm, the attenuation member 11 may be constituted by two graphite films each having a thickness of 20 µm stacked together or may be constituted by four graphite films each having a thickness of 10 µm stacked together.

The energy degrader 10 is periodically checked and replaced. In a case where the attenuation member 11 and a member near the attenuation member 11 have become radioactive at the time of replacement of the energy degrader 10, a worker is at a risk of exposure to radiation. Furthermore, in a case where these members become radioactive, disposal of these members as radioactive waste, for example, will be a problem. If the quantity of heat generated by the attenuation member 11 is large during usage of the energy degrader 10, the generated heat causes an increase in extent of radioactivation, and not only the attenuation member 11 but also members near the attenuation member 11 become radioactive. Therefore, preventing heat generation during the emission of a charged particle beam by employing an attenuation member 11 having a high heat dissipation performance is very important in order not only to merely increase the lifetime of the attenuation member 11 but also to prevent radioactivation.

(Method of Producing Graphite Film)

A method of producing a graphite film in accordance with the present embodiment is not particularly limited, and is, for example, a method of preparing a graphite film by treating a polymeric film with heat (e.g., by firing a polymeric film). Specifically, a method of producing a graphite film of one example of the present invention includes a carbonizing step and a graphitizing step.

<Carbonizing Step>

The carbonizing step involves carrying out carbonization by preheating an aromatic polyimide film, which is a starting material, under reduced pressure or in nitrogen gas. The preheating is carried out at a temperature from room temperature to 1500° C. The heat treatment temperature for carbonization needs to be at least 800° C. or above, and a heat treatment at preferably 900° C. or above, more preferably 1000° C. or above, is good in order to obtain highly plastic, highly heat-dissipating graphite. While temperature is raised, a pressure may be applied to the film along the thickness direction of the film to the extent that the film is not damaged, in order to prevent wrinkles from forming in the starting polymeric film.

<Graphitizing Step>

In the graphitizing step, graphitization may be carried out after removing the carbonized polyimide from a furnace and then transferring it to a graphitization furnace, or carbonization and graphitization may be carried out continuously. The graphitization is carried out under reduced pressure or in an inert gas. Suitable inert gases are argon and helium. The treatment may be carried out until the heat treatment temperature (firing temperature) reaches 2400° C. or above, preferably 2600° C. or above, more preferably 2800° C. or above. In the graphitizing step, a pressure may be applied along the thickness direction of the film.

According to the above method, it is possible to obtain a graphite film that has a good graphite crystal structure and that is highly thermally conductive.

The polymeric film for use in the present embodiment is a film of at least one polymer selected from polyimides, polyamides, polyoxadiazoles, polybenzothiazoles, polybenzobisthiazoles, polybenzoxazoles, polybenzobisoxasoles, polyparaphenylene vinylenes, polybenzimidazoles, polybenzobisimidazoles, and polythiazoles. A particularly preferable raw material film for the graphite film of the present invention is an aromatic polyimide film.

(Thermal Conductivity in Surface Direction of Graphite Film)

The thermal conductivity in a surface direction of a graphite film in the present embodiment is 1200 W/(m·K) or greater, preferably 1400 W/(m·K) or greater, more preferably 1600 W/(m·K) or greater, even more preferably 1800 W/(m·K) or greater.

From graphite films each having a thermal conductivity in the surface direction of 1200 W/(m·K) or greater, it is possible to obtain multilayer graphite having a better heat dissipation performance. A graphite film having a thermal conductivity in the surface direction of 1200 W/(m·K) or grater means that the thermal conductivity of this graphite film is equal to or greater than 3 times that of a metal material (for example, copper, aluminum).

Furthermore, the graphite film preferably has anisotropy (orientation) such that the thermal conductivity in the surface direction of the graphite film is equal to or greater than 50 times the thermal conductivity in the thickness direction of the graphite film.

The thermal conductivity in the surface direction of a graphite film is calculated using the following equation (1):

$$A = \alpha \times d \times Cp \tag{1}$$

where A represents the thermal conductivity in the surface direction of the graphite film, α represents the thermal diffusivity in the surface direction of the graphite film, d represents the density of the graphite film, and Cp represents the specific heat capacity of the graphite film. The thermal diffusivity in the surface direction, the density, and the specific heat capacity of the graphite film are obtained in the following manner.

The thermal diffusivity in the surface direction of a graphite film is measured in the following manner: a sample measuring 4 mm×40 mm cut from the graphite film is measured with the use of a measuring instrument using a light alternating-current method (for example, "LaserPIT" available from ULVAC RIKO, Inc.) in an atmosphere of 20° C. at a laser frequency of 10 Hz.

The density of a graphite film is measured in the following manner: a sample measuring 100 mm×100 mm cut from the graphite film is measured for weight and thickness; and the measured value of the weight is divided by the value of volume (calculated from 100 mm×100 mm×thickness).

The specific heat capacity of a graphite film is measured with the use of a differential scanning calorimeter DSC220CU, which is a thermal analysis system manufactured by SII NanoTechnology Inc., in the condition in which temperature is raised from 20° C. to 260° C. at 10° C./min.

The thermal conductivity in the thickness direction of the graphite film can be calculated in the same manner as described above using the foregoing equation (1), except that α in the equation is the thermal diffusivity in the thickness direction of the graphite film.

The thermal diffusivity in the thickness direction of the graphite film is determined by a pulse heating method (laser flash method). In this method, a laser is shined on one surface of the film and thereby the film is heated, and thereafter a temperature response (temperature change) at the opposite surface of the film is measured. Then, half-time ($t_{1/2}$), which is one-half of time (t) taken for the temperature to reach a certain temperature, is calculated using the following equation (2):

$$\alpha = \frac{d^2}{\tau_0} = 0.1388 \times \frac{d^2}{t_{1/2}} \tag{2}$$

where α represents thermal diffusivity, $\tau_0$ represents the period of thermal diffusion, d represents the thickness of a sample, $t_{1/2}$ represents half-time, and 0.1388 is the apparatus constant of the apparatus used.

(Thickness of Graphite Film)

The thickness of a graphite film in the present embodiment is 0.1 μm or greater and 50 μm or less, more preferably 0.2 μm or greater and 40 μm or less, more preferably 0.4 μm or greater and 30 μm or less, particularly preferably 0.8 μm or greater and 20 μm or less. The graphite film having such a thickness is preferred, because, even upon beam irradiation, the attenuation member 11 is less likely to become radioactive.

The thickness of a graphite film is measured in the following manner: thicknesses at any ten locations of a film measuring 50 mm×50 mm cut from the graphite film are measured in a thermostatic chamber at 25° C. with the use of a thickness gage (HEIDENHAIN-CERTO, manufactured by HEIDENHAIN); and the mean of the thicknesses is used as the thickness of the graphite film.

(Electric Conductivity in Surface Direction of Graphite Film)

The electric conductivity in the surface direction of a graphite film in the present embodiment is not particularly limited, and is preferably 12000 S/cm or greater, preferably 14000 S/cm or greater, more preferably 16000 S/cm or greater, more preferably 18000 S/cm or greater, more preferably 20000 S/cm or greater.

Furthermore, the graphite film preferably has anisotropy (orientation) such that the electric conductivity in the surface direction of the graphite film is equal to or greater than 100 times the electric conductivity in the thickness direction of the graphite film.

The electrical conductivity of a graphite film is measured by applying a constant current in a four-point probe method (for example, by using Loresta-GP, manufactured by Mitsubishi Chemical Analytech Co., Ltd.)

(Density of Graphite Film)

The density of a graphite film in the present embodiment is not particularly limited, and is preferably 1.40 g/cm³ or greater, preferably 1.60 g/cm³ or greater, more preferably 1.80 g/cm³ or greater, more preferably 2.00 g/cm³ or greater, more preferably 2.10 g/cm³ or greater. A graphite film having a density of 1.40 g/cm³ or greater is preferred, because such a graphite film has an excellent self-supporting property and excellent mechanical strength properties.

Furthermore, since a graphite film having a greater density has a higher possibility of interacting with a charged particle beam, a graphite film having a high density is highly effective as an energy degrader. In addition, a graphite film having a high density has little gap between its constituent graphite layers, and therefore such a graphite film tends to have a high thermal conductivity. In a case where a graphite film has a low density, such a graphite film has a poor efficiency in decelerating a charged particle beam, and, in addition, the graphite film also has a decreased thermal conductivity due to the effects of air layers between the constituent graphite layers. This is therefore not preferred. It is also inferred that, in the air layers (hollow portions), thermal conductivity is poor and thus heat is likely to be trapped in these portions. Therefore, a graphite film having a low density easily deteriorates. Furthermore, in a case where a graphite film has a high density, a charged particle beam is less likely to be scattered when passing through the graphite film. Therefore, in the case of a graphite film having a high density, a charged particle beam is less likely to be scattered even in a case where such graphite films are stacked together. In view of these matters, the graphite film preferably has a high density. The density is preferably 1.40 g/cm³ or greater, preferably 1.60 g/cm³ or greater, more preferably 1.80 g/cm³ or greater, more preferably 2.00 g/cm³ or greater, more preferably 2.10 g/cm³ or greater. In regard to the upper limit of the density of the graphite film, the density of the graphite film is 2.26 g/cm³ (theoretical value) or less, and may be 2.20 g/cm³ or less.

The density of a graphite film is measured in the following manner: a sample measuring 100 mm×100 mm cut from the graphite film is measured for weight and thickness; and the measured value of the weight is divided by the value of volume (calculated from 100 mm×100 mm×thickness).

(MIT Folding Endurance of Graphite Film)

The number of times a graphite film is folded in an MIT folding endurance test for the graphite film may be preferably 500 or more, more preferably 1000 or more, even more preferably 5000 or more, particularly preferably 10000 or more.

The MIT folding endurance test for a graphite film is carried out in the following manner. Three test pieces each measuring 1.5×10 cm are removed from the graphite film. The test is carried out with the use of an MIT crease-flex fatigue resistance tester Model D manufactured by Toyo Seiki Seisaku-sho, Ltd. under the conditions in which test load is 100 gf (0.98 N), speed is 90 times/min., and radius of curvature R of folding clamp is 2 mm. The graphite film is folded to an angle of 135° in either direction in an atmosphere of 23° C., and the number of times the graphite film is folded before the graphite film is severed is counted.

(Regarding Energy of Charged Particle Beam in the Present Embodiment)

In the energy degrader 10, a charged particle beam passes through the attenuation member 11 constituted by a graphite film. The energy of the charged particle beam passing through the attenuation member 11 is relatively low. The collision stopping power (energy loss) of a target material (in this case, the attenuation member 11) for a charged particle is represented by the following Bethe equation (equation (3)):

$$S_{col} = -\frac{4\pi e^4 z^2 N}{mv^2} Z \left[ \ln \frac{2mv^2}{I(1-\beta^2)} - \beta^2 \right] \quad (3)$$

where e represents elementary charge of electron, m represents mass of electron, v represents velocity of electron, z represents nuclear charge of incident particle, Z represents the atomic number of the target material, N represents the number of atoms per unit volume of the target material, I represents the mean excitation potential of the target material, and β represents v/c where c is the speed of light.

Figure 3:
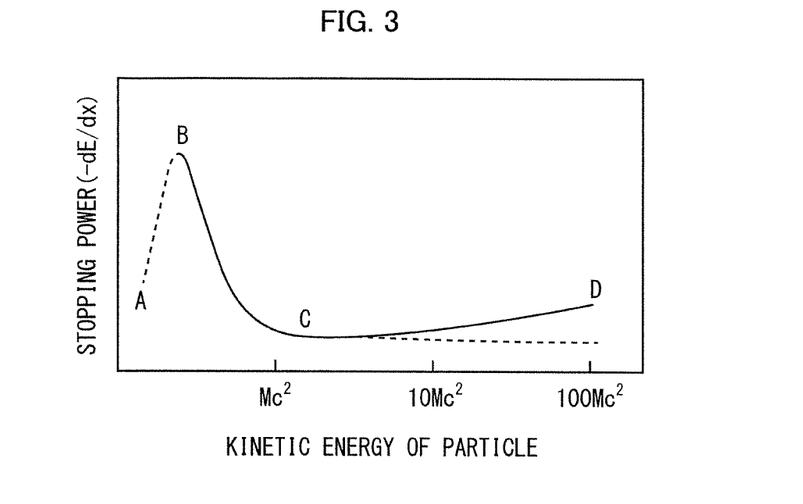
FIG. 3 is a graph showing the relationship between stopping power based on the Bethe equation and kinetic energy of particle.

FIG. 3 is a graph showing the relationship between the stopping power based on the Bethe equation (equation (3)) and kinetic energy of particle. As illustrated in FIG. 3, the collision stopping power (energy loss) of a target material for a charged particle increases from A (kinetic energy of particle is low) to B and reaches maximum at B. Then, the stopping power decreases from B to C in proportional to $I/v^2$, and reaches minimum at C. Then, the stopping power gradually increases from C to D, where logarithms of the Bethe equation (equation (3)) are effective.

The charged particle beam, which is to be attenuated by the energy degrader 10 in accordance with the present embodiment, is a charged particle beam whose energy falls within the energy range of B to C, and thus has a relatively low energy. The energy of the charged particle beam at B is on the order of MeV (for example, 1 MeV), and the energy of the charged particle beam at C is on the order of GeV (for example, 3 GeV). The stopping power of the target material at B is about 100 times as high as the stopping power of the target material at C.

Therefore, the energy degrader 10 for use in the present embodiment is required to be about 100 times as durable as an attenuation member for use for an accelerator which accelerates a charged particle beam whose energy falls within the energy range of C to D (for example, energy of 3 GeV or greater), provided that the number of charged particles is the same. The number of charged particles differs depending on the intended use of each accelerator, and therefore the energy degrader 10 is not always required to be 100 times as durable. However, in the energy range of 1 to 100 MeV of a small accelerator for cancer treatment, which is the major application of the present embodiment, the energy degrader 10 is undoubtedly required to be far more durable than that for use for a high-energy accelerator for 3 GeV or greater.

Under such severe conditions, the graphite film of the energy degrader in accordance with the present embodiment can satisfy the above required durability despite the foregoing thickness.

(Modified Example of Energy Degrader)

The following description will discusses a modified version of the energy degrader in accordance with the present embodiment. The energy degrader in accordance with the present embodiment may include an attenuation structure constituted by a plurality of attenuation members. Each attenuation member is, as described earlier, constituted by a graphite film which is placed such that a charged particle is incident on a surface of the graphite film. The attenuation structure has a multilayer structure, in which the plurality of attenuation members are stacked together along the thickness direction. The graphite film constituting each attenuation member is not limited, provided that the graphite film has the foregoing properties.

A charged particle beam, such as an ion beam or a proton beam, needs to be more precisely controlled depending on the stage of a patient's disease and/or the position of an affected area. In a case where irradiation with too intense an ion beam is carried out, or in a case where an area other than the affected area is irradiated with a beam, this may worsen the condition of the patient or may slow down the recovery of the patient.

In view of this, it is very important for a particle beam therapy system to strictly control the intensity of a beam with which a patient is irradiated. In a case where the intensity of a charged particle beam is to be controlled at a desired intensity, the thickness of an attenuation structure through which the charged particle beam passes is precisely controlled. In a case where the attenuation structure is a usual graphite block or a graphite disk, the thickness of the attenuation structure is adjusted through a precision machining process, a grinding process, and/or the like. This makes the adjustment of the thickness of the attenuation structure complicated.

On the other hand, according to the foregoing arrangement of the energy degrader, the attenuation structure has a multilayer structure in which a plurality of attenuation members are stacked together along the thickness direction. Furthermore, each attenuation member is constituted by a graphite film which is placed such that a charged particle beam is incident on a surface of the graphite film. Therefore, by stacking together attenuation members constituted by graphite films, it is possible to easily obtain an attenuation structure having a desired thickness.

When the attenuation structure is irradiated with a charged particle beam, damage on its outermost graphite portion is severe. In a case where the attenuation structure is a usual graphite disk, the whole graphite disk needs to be replaced if the damage to the outermost graphite portion is severe.

In contrast, according to the foregoing arrangement of the energy degrader, since the attenuation structure has a multilayer structure in which a plurality of attenuation members are stacked together along the thickness direction, it is only necessary to replace several outer attenuation members including the damaged outermost attenuation member. As such, the attenuation structure in the present embodiment is very good also for economic reasons.

The optimal thickness of the attenuation structure differs depending on the intensity of a charged particle beam, type of charged particle beam (ionic species), and the like, and is determined as appropriate.

As has been described, according to the energy degrader in accordance with the modified version of the present embodiment, the attenuation structure is configured to be flexibly adjustable to every thickness. Therefore, it is possible to easily control the thickness of the attenuation structure in order to control the intensity of a charged particle beam, such as an ion beam, at a desired intensity. For example, even in a case where an attenuation structure having a thickness of 100 μm or greater is intended, such an attenuation structure can be flexibly obtained by stacking together a plurality of attenuation members constituted by graphite films.

The plurality of attenuation members constituting the attenuation structure may have the same thickness or may have different thicknesses, provided that the thickness of each attenuation member is 0.1 μm or greater and 50 μm or less. The number of attenuation members constituting the multilayer structure of the attenuation structure is not particularly limited, and is preferably 100 or less.

The multilayer structure of the attenuation structure may be such that each of the attenuation members constituting the multilayer structure is removably provided in the attenuation structure. With this arrangement in which each attenuation member is removably provided in the attenuation structure, it is possible to easily adjust the thickness of the attenuation structure and also possible to obtain attenuation structures having various thicknesses. A preferred embodiment of the multilayer structure is a structure in which the attenuation members are stacked together with no adhesive between them and the stacked attenuation members are physically maintained by a retainer or the like.

Alternatively, the multilayer structure of the attenuation structure may be arranged such that the attenuation members constituting the attenuation structure have a gap between them. In such a case in which the attenuation members have a gap between them, the thickness of the gap is not included in the thickness of the attenuation structure.

The multilayer structure of the attenuation structure may vary in thickness along the surface direction which intersects the path of a proton beam. Examples of such a shape of the multilayer structure include: bowl shape in which the thickness along the surface direction decreases with decreasing distance to the center of an attenuation member; and stepped shape as illustrated in FIG. 4.

Figure 4:
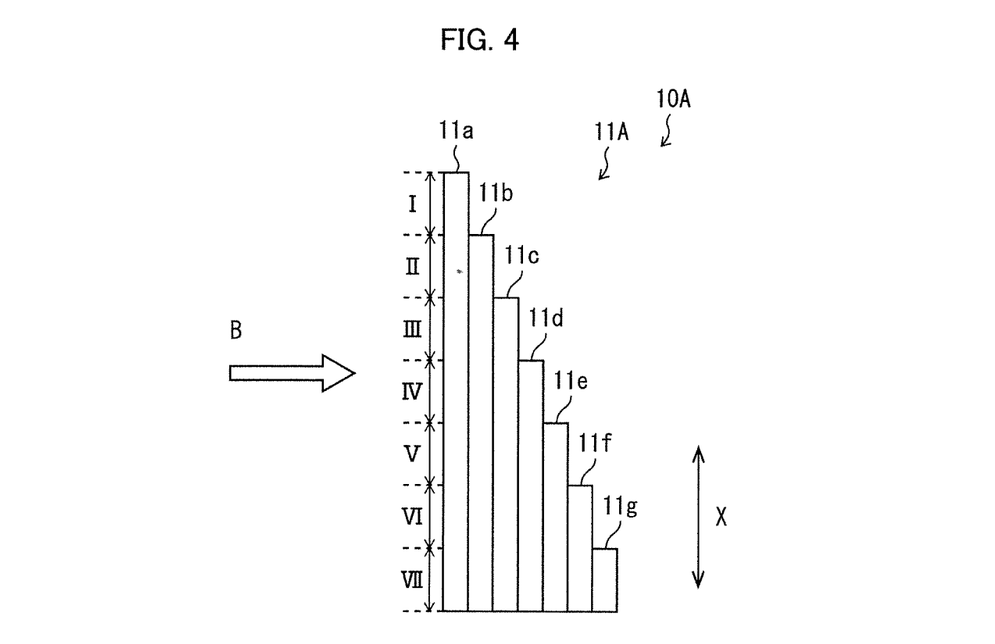
FIG. 4 schematically illustrates a modified example of the energy degrader 10 in accordance with an embodiment of the present invention.

FIG. 4 schematically illustrates an example of a configuration of an energy degrader in accordance with a modified version of the present embodiment. As illustrated in FIG. 4, an energy degrader 10A, serving as a modified example, includes an attenuation structure 11A constituted by a plurality of attenuation members 11a to 11g configured to attenuate the energy of a proton beam B which passes through the attenuation members 11a to 11g. The energy (speed) of charged particles of an accelerated beam is decelerated to an extent that depends on the thickness of a graphite film(s), which is an attenuation member for attenuating the energy. Therefore, with the arrangement as illustrated in FIG. 4, it is possible to decelerate the energy (speed) of charged particles of an accelerated beam to a preferred extent.

A thickness of the attenuation structure 11A is 1 μm or greater and 200 μm or less, more preferably 2 μm or greater and 150 μm or less, particularly preferably 5 μm or greater and 100 μm or less.

The attenuation members 11a to 11g are constituted by graphite films and, when seen in one direction, have respective different dimensions. In the present embodiment, the attenuation members 11a to 11g have respective different dimensions when seen in an X direction, which intersects the path of the proton beam B. The attenuation members 11a to 11g are stacked together, for example, such that they are aligned at one of the opposite ends along the X direction and that their dimensions along the X direction decrease progressively in the direction in which the proton beam B travels. The attenuation members 11a to 11g stacked together in this manner give the following arrangement. The attenuation structure 11A has a stepped shape such that the attenuation structure 11A's thickness along the X direction progressively decreases. When considered based on zones I to VII into which the surface that receives the proton beam B is divided, the attenuation structure 11A has a stepped shape such that the thickness of the attenuation structure 11A progressively increases from zone I to zone VII. Note that the attenuation members 11a to 11g may alternatively be stacked together such that their dimensions along the X direction progressively increase in the direction in which the proton beam B travels.

The energy degrader 10A is configured to change the extent to which the energy of the proton beam B is attenuated, by moving, into the path of the proton beam B, any of zones I to VII of the attenuation structure 11A through which the proton beam B passes. The energy degrader 10A decelerates the proton beam B to an extent that depends on the thickness of the attenuation structure 11A through which the proton beam B passes. The proton beam B is reduced in kinetic energy and thus is attenuated.

Note, here, that the energy degrader 10A may have, at a position outside the attenuation structure 11A and beside zone VII, a highly permeable zone constituted by a material that is permeable to the proton beam B to a greater extent than the graphite film. The highly permeable zone is thicker than zone VII of the attenuation structure 11A, and attenuates energy to a greater extent than zone VII. The highly permeable zone is made from a substance whose atomic number is less than that of carbon. This is because an attenuation material having a higher atomic number causes a greater scattering of the proton beam B and thus the number of protons that can pass through the material decreases. A specific example of a material for the highly permeable zone is beryllium (Be), which is a stable solid substance with a low atomic number.

The proton beam B, which has passed through the energy degrader 10A, is introduced into the rotatable gantry 3 via the ESS 30 and the transport line 4, and then is emitted toward an irradiation target. In this way, the proton beam B is emitted so that the proton beam B is delivered to a position at a certain depth in the irradiation target.

According to a particle beam therapy system 1 which includes the energy degrader 10A, it is possible to: reduce the extent of attenuation by the energy degrader 10A in a case of emitting the proton beam B so that the proton beam B is delivered to a position deep inside the irradiation target; and increase the extent of attenuation by the energy degrader 10A in a case of emitting the proton beam B so that the proton beam B is delivered to a shallow position (for example, near body surface) inside the irradiation target.

In a case where the attenuation structure 11A of the energy degrader 10A has the foregoing highly permeable zone, since the zone that attenuates energy to the greatest extent is constituted by beryllium, it is possible to prevent a decrease in number of protons that pass through the highly permeable zone while preventing an increase in production cost. That is, it is possible to prevent a decrease in number of protons to be emitted. This makes it possible to effectively deliver the proton beam B to a shallow position near the body surface, and thus possible to obtain a highly reliable particle beam therapy system 1.

The arrangement illustrated in FIG. 4 is such that the attenuation members 11*a* to 11*g* have respective different dimensions when seen in the X direction, which intersects the path of the proton beam B. Note, however, that the attenuation members 11*a* to 11*g* are not limited to the arrangement illustrated in FIG. 4, and may have, for example, the same dimension when seen in the X direction which intersects the path of the proton beam B. In this case, the attenuation structure 11A is structured such that the faces of zones I to VII, on which the proton beam B incident, are flush with each other along the X direction.

The present invention is not limited to the embodiments, but can be altered by a skilled person in the art within the scope of the claims. The present invention also encompasses, in its technical scope, any embodiment derived by combining technical means disclosed in differing embodiments.

[Recap]

The radioactivation of an attenuation member is caused by an interaction between an ion beam passing through the attenuation member and atoms inside the attenuation member, and therefore the extent of the radioactivation is related to the atomic density of the attenuation member, i.e., the specific gravity of the attenuation member. Carbon (light element) materials do not easily become radioactive due to their small specific gravity. For example, the specific gravity of titanium is 4.51, and the specific gravity of carbon (graphite) is 2.26. However, a film made of a carbon material is generally inferior to metal films in their properties such as durability, mechanical strength, and heat resistance, and therefore needs to be sufficiently thick to be used as an attenuation member. On the other hand, in a case where a thick carbon film is used, a strong interaction occurs between the beam and the atoms inside the material as described earlier, and this results in loss of the superior characteristics (i.e., not easily become radioactive) of an energy degrader made of a carbon material.

The inventors studied hard about an attenuation member constituted by graphite in search of an arrangement with which the extent of radioactivation is small, and found that it is possible to solve the issues of durability and heat resistance of the graphite by using a graphite film having specific properties as a graphite film constituting the attenuation member, and that it is possible to reduce the extent of radioactivation by reducing the thickness of the graphite film. On the basis of these findings, the inventors accomplished the present invention.

Specifically, in order to attain the foregoing object, an energy degrader in accordance with one aspect of the present invention is an energy degrader including one or more attenuation members configured to attenuate energy of a charged particle beam incident thereon, wherein at least one of the one or more attenuation members is a graphite film placed such that the charged particle beam is incident on a surface thereof, the graphite film has a thermal conductivity, in a surface direction, of 1200 W/(m·K) or greater, and the graphite film has a thickness of 0.1 μm or greater and 50 μm or less.

According to the above arrangement, at least one of the one or more attenuation members is a graphite film placed such that the charged particle beam is incident on a surface thereof, the graphite film has a thermal conductivity, in a surface direction, of 1200 W/(m·K) or greater, and the graphite film has a thickness of 0.1 μm or greater and 50 μm or less. This makes it possible to dramatically reduce the extent of radioactivation of the attenuation member(s) as compared to conventional energy degraders.

The energy degrader in accordance with one aspect of the present invention is preferably arranged such that the thermal conductivity in the surface direction of the graphite film is equal to or greater than 50 times a thermal conductivity in a thickness direction of the graphite film. As such, the graphite film constituting the attenuation member of the energy degrader of the present invention has a high orientation and a high anisotropy in thermophysical property.

The energy degrader in accordance with one aspect of the present invention is preferably arranged such that an electric conductivity in the surface direction of the graphite film is 12000 S/cm or greater.

The energy degrader in accordance with one aspect of the present invention is preferably arranged such that an electric conductivity in the surface direction of the graphite film is equal to or greater than 100 times an electric conductivity in a thickness direction of the graphite film.

The energy degrader in accordance with one aspect of the present invention is preferably arranged such that the graphite film has a density of 1.40 g/cm$^3$ or greater and 2.26 g/cm$^3$ or less.

An energy degrader in accordance with another aspect of the present invention is an energy degrader including an attenuation structure constituted by a plurality of attenuation members each configured to attenuate energy of a charged particle beam incident thereon, the attenuation structure having a multilayer structure composed of the plurality of attenuation members stacked together along a thickness direction, the plurality of attenuation members being constituted by graphite films each placed such that the charged particle beam is incident on a surface thereof.

The energy degrader in accordance with another aspect of the present invention is preferably arranged such that the multilayer structure varies in thickness along a surface direction.

According to the above arrangement, the attenuation structure has a multilayer structure composed of a plurality of attenuation members stacked together along the thickness direction. Furthermore, the attenuation members are constituted by graphite films each placed such that the charged particle beam is incident on a surface thereof. As such, by stacking together the attenuation members constituted by graphite films, it is possible to easily obtain an attenuation structure having a desired thickness.

The energy degrader in accordance with another aspect of the present invention is preferably arranged such that the multilayer structure has a stepped shape and progressively increases in thickness along the surface direction from one side of the attenuation structure to the other side of the attenuation structure, the one side and the other side being parallel to a surface on which the charged particle beam is incident.

As the thickness of a graphite film serving as an attenuation member changes, the energy (speed) of a charged particle beam also changes. Therefore, use of the above arrangement makes it possible to obtain a preferred energy (speed) of the charged particle beam.

In order to attain the foregoing object, a charged particle emission system in accordance with a further aspect of the present invention is a charged particle emission system including the foregoing energy degrader and configured to emit the charged particle beam, the charged particle emission system including: an accelerator configured to accelerate charged particles which are to enter the energy degrader; and an emission device configured to emit the charged particle beam whose energy has been attenuated by the energy degrader.

The charged particle emission system arranged like above is sufficiently durable and heat-resistant as compared to conventional charged particle emission systems and, in addition, the extent of radioactivation of the attenuation member is dramatically reduced as compared to conventional charged particle emission systems.

In order to attain the foregoing object, a method of producing a graphite film in accordance with still a further aspect of the present invention is a method of producing a graphite film for use as an attenuation member of an energy degrader, the method including firing a polymeric film at a temperature of 2400° C. or above to obtain the graphite film.

This makes it possible to produce an attenuation member that becomes radioactive to a much lesser extent than those of conventional energy degraders.

INDUSTRIAL APPLICABILITY

The present invention can be used in technical fields in which an accelerator is used, in particular, in the fields of cancer treatment using positrons.

REFERENCE SIGNS LIST

1 Particle beam therapy system (charged particle emission system)
10, 10A Energy degrader
2 Cyclotron
3 Rotatable gantry
4 Transport line
11, 11a to 11g Attenuation member
11A Attenuation structure

The invention claimed is:

1. An energy degrader comprising one or more attenuation members configured to attenuate energy of a charged particle beam incident thereon, wherein
at least one of the one or more attenuation members is a graphite film placed such that the charged particle beam is incident on a surface thereof,
the graphite film has a thermal conductivity, in a surface direction, of 1200 W/(m·K) or greater,
the graphite film has a thickness of 0.1 μm or greater and 50 μm or less, and
the charged particle beam is a proton beam.

2. The energy degrader according to claim 1, wherein the thermal conductivity in the surface direction of the graphite film is equal to or greater than 50 times a thermal conductivity in a thickness direction of the graphite film.

3. The energy degrader according to claim 1, wherein an electric conductivity in the surface direction of the graphite film is 12000 S/cm or greater.

4. The energy degrader according to claim 1, wherein an electric conductivity in the surface direction of the graphite film is equal to or greater than 100 times an electric conductivity in a thickness direction of the graphite film.

5. The energy degrader according to claim 1, wherein the graphite film has a density of 1.40 $g/cm^3$ or greater and 2.26 $g/cm^3$ or less.

6. An energy degrader comprising
an attenuation structure constituted by a plurality of attenuation members each configured to attenuate energy of a charged particle beam incident thereon,
the attenuation structure having a multilayer structure composed of the plurality of attenuation members stacked together along a thickness direction, the plurality of attenuation members being constituted by graphite films each placed such that the charged particle beam is incident on a surface thereof;
the graphite film has a thermal conductivity, in a surface direction, of 1200 W/(mK) or greater,
the graphite film has a thickness of 0.1 μm or greater and 50 μm or less; and
the charged particle beam is a proton beam.

7. The energy degrader according to claim 6, wherein the multilayer structure varies in thickness along a surface direction.

8. The energy degrader according to claim 7, wherein the multilayer structure has a stepped shape and progressively increases in thickness along the surface direction from one side of the attenuation structure to the other side of the attenuation structure, the one side and the other side being parallel to a surface on which the charged particle beam is incident.

9. A charged particle emission system comprising the energy degrader recited in claim 1 and configured to emit the charged particle beam, the charged particle emission system comprising:
an accelerator configured to accelerate charged particles which are to enter the energy degrader; and
an emission device configured to emit the charged particle beam whose energy has been attenuated by the energy degrader.

10. A charged particle emission system comprising the energy degrader recited in claim 6 and configured to emit the charged particle beam, the charged particle emission system comprising:
an accelerator configured to accelerate charged particles which are to enter the energy degrader; and
an emission device configured to emit the charged particle beam whose energy has been attenuated by the energy degrader.

11. The energy degrader according to claim 1, wherein the energy of the charged particle beam ranges from 1 MeV to 3 GeV before attenuation.

12. A method of attenuating the energy of a proton beam, the method comprising:
allowing the proton beam having an energy within the range of from 1 MeV to 3 GeV to incident on a surface of a graphite film,
wherein the graphite film has a thermal conductivity, in a surface direction of 1200 W/(m K) or greater, and
wherein the graphite film has a thickness of 0.1 μm or greater and 50 μm or less.

* * * * *